United States Patent
Thai

(10) Patent No.: US 8,690,571 B2
(45) Date of Patent: Apr. 8, 2014

(54) ANTI-ROTATION INSTRUMENT

(76) Inventor: Hung M. Thai, San Jose, CA (US)

(*) Notice: Subject to any disclaimer, the term of this patent is extended or adjusted under 35 U.S.C. 154(b) by 12 days.

(21) Appl. No.: 13/604,369

(22) Filed: Sep. 5, 2012

(65) Prior Publication Data

US 2014/0065572 A1    Mar. 6, 2014

(51) Int. Cl.
*A61C 3/00* (2006.01)

(52) U.S. Cl.
USPC .......................................................... 433/147

(58) Field of Classification Search
USPC ............. 433/72, 147, 75, 141, 142, 143, 144, 433/172–176
See application file for complete search history.

(56) References Cited

U.S. PATENT DOCUMENTS

| | | | | |
|---|---|---|---|---|
| 631,732 A * | 8/1899 | Ivory | | 417/134 |
| 2,604,693 A * | 7/1952 | Schierstead | | 30/152 |
| 4,251,214 A * | 2/1981 | Schnall | | 433/147 |
| 4,677,985 A * | 7/1987 | Bro et al. | | 600/504 |
| 5,246,370 A * | 9/1993 | Coatoam | | 433/173 |
| 6,109,918 A * | 8/2000 | Hammond et al. | | 433/141 |
| 6,997,709 B2 * | 2/2006 | Kangasniemi et al. | | 433/147 |
| 2007/0031788 A1 * | 2/2007 | Chao | | 433/144 |
| 2008/0124674 A1 * | 5/2008 | Meuchel | | 433/141 |

* cited by examiner

*Primary Examiner* — Cris L Rodriguez
*Assistant Examiner* — Mirayda A Aponte

(57) ABSTRACT

The present invention features an anti-rotation instrument system which could be applied/used in all health professions such as medical, dental, and any other specialties. The system includes an anti-rotation instrument device comprising a main handle, a first removable hand grip and a first instrumental tip. The first removable hand grip is attached to a first female screw cavity disposed on the main handle. One end of the instrumental tip passes through a channel disposed within first hand grip with an anti-rotation key disposed on the instrumental tip securely reside within a dent disposed on the distal end of the first removable hand grip and the threading disposed on the end of the instrumental tip is subsequently screwed into the first female screw cavity of the main handle such that the first hand grip is tightly sandwiched between the first instrumental tip and main body.

15 Claims, 3 Drawing Sheets

ANTI-ROTATION INSTRUMENT

FIELD OF THE INVENTION

The present invention related to an anti-rotation instrument which could be applied/used in all health professions such as medical, dental, and any other specialties.

BACKGROUND OF THE INVENTION

Many medical or dental handles have an instrument tip, such as dental probe tip, soldered to the handle. With this design, the surgeon will have to buy a whole new instrument if his instrument tip is broken or worn out. Some medical or dental handles has the instrument tip screwed into the handle. With this design, the tip could unscrew itself from the handle during surgery which could pose a potential safety issue; such as, when the surgeon uses this intra-oral mirror to retract patients' tongue during surgical procedure. If the mirror head become loosen which the tongue could slip and got cut. Hence, there is a need for a medical or dental handles with a replaceable tip and with anti-rotation function during usage.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

The present invention features an anti-rotation instrument system which could be applied/used in all health professions such as medical, dental, and any other specialties. The device includes a main handle, a first removable hand grip and a first instrumental tip. The first removable hand grip is attached to a first female screw cavity disposed on the main handle. One end of the instrumental tip passes through a channel disposed within first hand grip with an anti-rotation key disposed on the instrumental tip securely reside within a dent disposed on the distal end of the first removable hand grip and the threading disposed on the end of the instrumental tip is subsequently screwed into the first female screw cavity of the main handle such that the first hand grip is tightly sandwiched between the first instrumental tip and main body.

DESCRIPTION OF PREFERRED EMBODIMENTS

Figure 1:
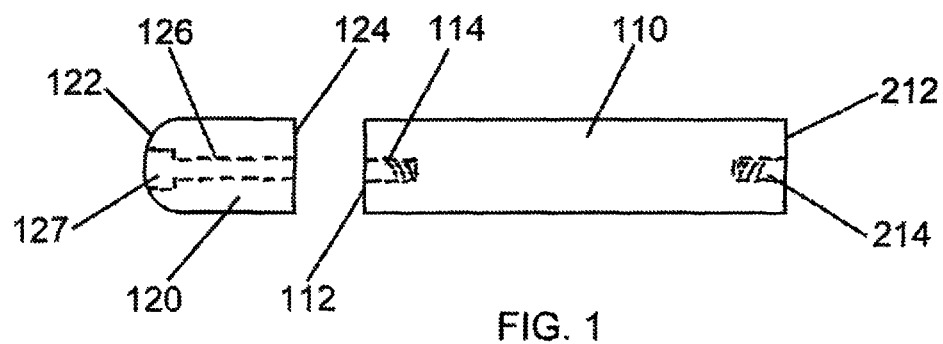
FIG. 1 shows a main body and a first removable hand grip.
Figure 2:
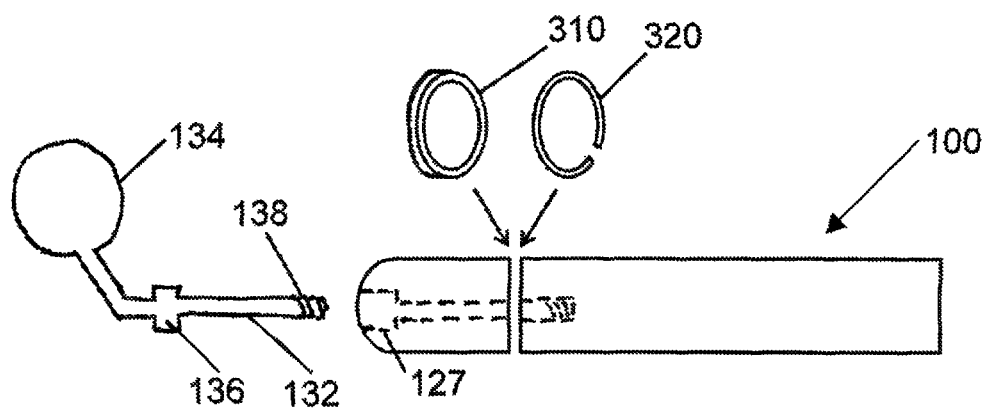
FIG. 2 shows a main body, a first removable hand grip and a first instrumental tip.
Figure 3:
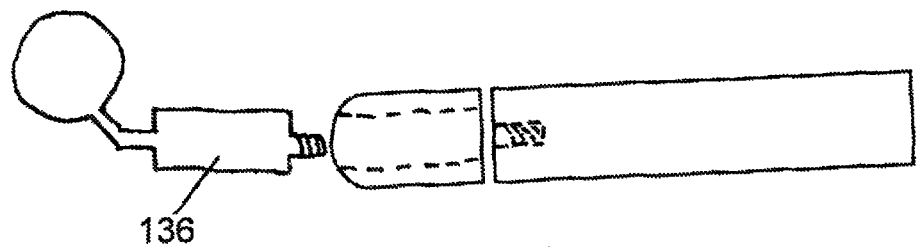
FIG. 3 shows an alternative embodiment of a main body, a first removable hand grip and a first instrumental tip.
Figure 4:
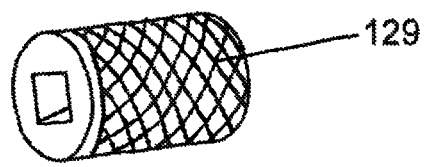
FIG. 4 shows a grip layer disposed on the removable hand grip.
Figure 5:
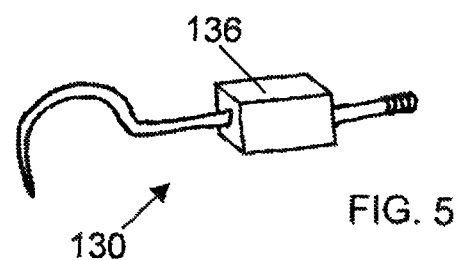
FIG. 5 shows an alternative embodiment of the instrumental tip.
Figure 6:
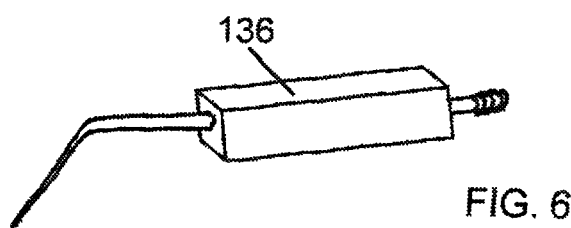
FIG. 6 shows a third alternative embodiment of the instrumental tip.

Referring now to FIG. 1-10, the present invention features an anti-rotation instrument system which could be applied/used in all health professions such as medical, dental, and any other specialties. The system includes an anti-rotation instrument device (100) comprising a main handle (110), a first removable hand grip (120), and a first instrumental tip (130). The first removable hand grip (120) is attached to a first female screw cavity (114) disposed on the main handle. One end of the instrumental tip passes through a channel (126) disposed within first hand grip (120) with an anti-rotation key (136) disposed on the instrumental tip securely reside within the first dent (127) disposed on the distal end of the first removable hand grip (120) and wherein the threading (138) is subsequently screwed into the first female screw cavity (114) of the main handle (110) such that the first hand grip (120) is tightly sandwiched between the first instrumental tip (130) and main body (110).

The anti-rotation instrument device (100) comprises a main handle (110), a first removable hand grip (120), and a first instrumental tip (130). The main handle has a first end (112) and a second end (212), wherein a first female screw cavity (114) is disposed on the first end. The removable hand grip (120) has a distal end (122) and a proximal end (124), wherein a channel (126) is disposed through the hand grip extending from the distal end to the proximal end, wherein a first dent (127) is disposed on the distal end of the first removable hand grip and extend at least a portion of the channel (126). The first instrumental tip (130) has a first end (134) and a second end (132), wherein the second end (132) has a threading (138) disposed at the second end, wherein the threading (138) matches said female screw cavity (114), wherein a first anti-rotation key (136) is disposed on the first instrumental tip between the first end (134) and second end (132), wherein the first anti-rotation key (136) is adaptive to snuggly fit the first dent (127) disposed on the distal end of the first removable hand grip.

The second end (132) of the instrumental tip (130) passes through the channel (126) of first hand grip (120) with the first anti-rotation key (136) securely reside within the first dent (127) disposed on the distal end of the first removable hand grip (120) and wherein the threading (138) is subsequently screwed into the first female screw cavity (114) of the main handle (110) such that the first hand grip (120) is tightly sandwiched between the first instrumental tip (130) and main body (110).

In some embodiments, the system further comprises a washer (310) or a spring washer (320), wherein the washer (310) or spring washer (320) are disposed between the main body and the removable handgrip (120). In some embodiments, the washer (310) is made of rubber or stainless steel. In some embodiments, the second end (132) of the instrumental tip (130) is made from surgical grade stainless steel or fiberglass or acrylic, or a combination thereof.

In some embodiments, the first end (134) of the first instrumental tip (130) is any dental/medical instrument tip, for example, a mirror or a dental sickle probe or a periodontal probe. The anti-rotation key (136) is any non-rotatable key, such as for example, flat key, rectangle key, hex key, square key or oval key. In some embodiments, the anti-rotation key (136) is any non-round key that allows for catching or fixing within the dent to prevent spinning of the key or the instrumental tip.

In some embodiments, the first dent (127) extends throughout of the channel (126) of the first removable hand grip (120). In some embodiments, the first anti-rotation key (136) has a length (137) equal to the length of the channel (130).

In some embodiments, the main body (110) has a cylindrical shape and the first removable hand grip (120) has also a cylindrical shape. In some embodiments, the first removable hand grip (120) has a grip layer (129) disposed on exterior surface. In some embodiments, the grip (129) has a dot or line, pattern disposed on grip surface for grip enhancement. In some embodiments, the grip (129) may be round with a rough surface for gripping. In some embodiments, the grip (129) may be an irregular shape (or non-round shape) with or without a rough surface. In some embodiments, the grip layer (129) is made from stainless steel or rubber. In some embodiments, the grip pattern is done by embossing during hand grip manufacturing.

In some embodiments, the system further comprises a first bulge (116) disposed on the first end (112) of the main body (110) and a second dent disposed on the proximal end of the first removable grip (120). The first female screw cavity (114) passes through the first bulge (116) and the second dent (128) is adaptive to snuggly fit the first bulge (116).

The second end (132) of the instrumental tip (130) passes through the channel (126) of first hand grip (120) with the first anti-rotation key (136) securely reside within the first dent (127) disposed on the distal end of the first removable hand grip (120) and wherein the threading (138) is subsequently screwed into the first female screw cavity (114) of the main handle (110) such that the first bulge (116) is snuggly fitted into the second dent (128) of the first removable grip (120) and such that the first hand grip (120) is tightly sandwiched between the first instrumental tip (130) and main body (110).

Figure 7:
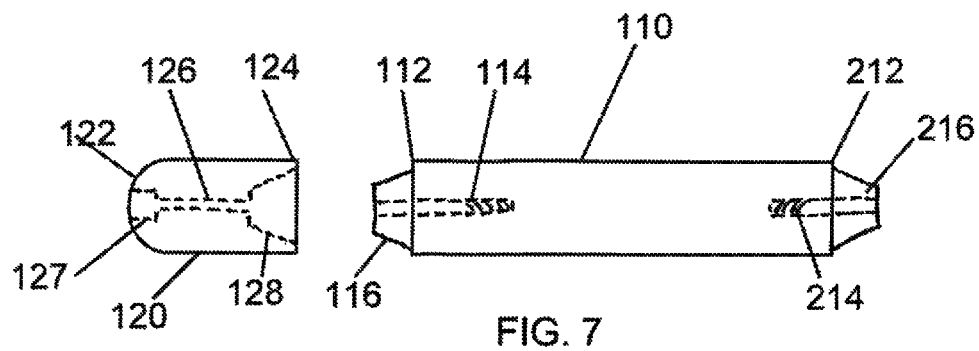
FIG. 7 shows a third alternative embodiment of a main body, a first removable hand grip and a first instrumental tip.
Figure 8:
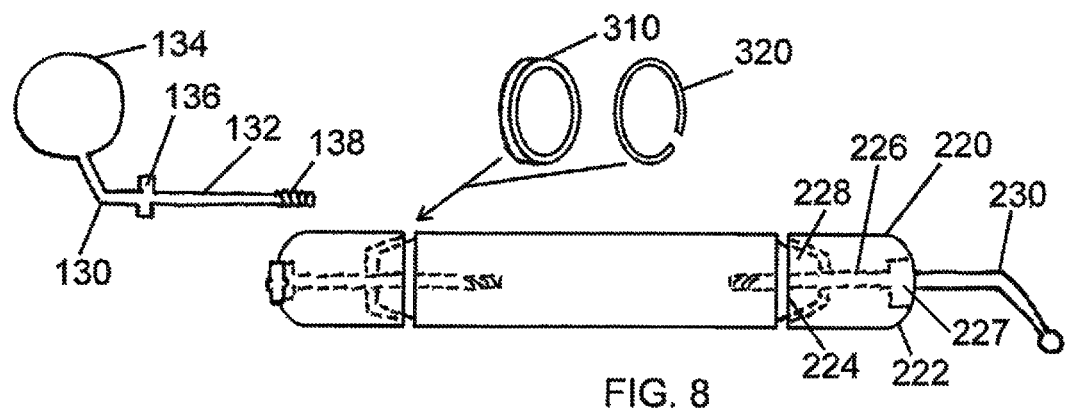
FIG. 8 shows a fourth alternative embodiment of a main body, a first removable hand grip, a first instrumental tip, a second removable hand grip and a second instrumental tip.
Figure 9:
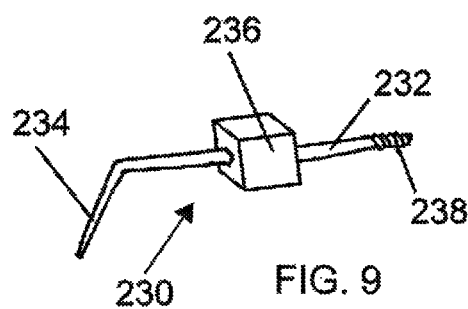
FIG. 9 shows a fourth alternative embodiment of the instrumental tip.
Figure 10:
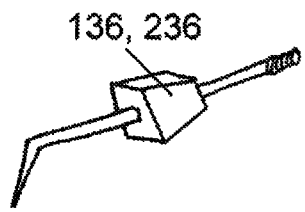
FIG. 10 shows a fifth alternative embodiment of the instrumental tip.

In some embodiments, the second end (212) of the main body (110) has similar configuration as the first end (112) with a female screw cavity for the attachment of a second hand grip and a second instrumental tip. The second tip can be the same or different from the first instrumental tip, as shown in FIGS. 7-8.

In some embodiments, the anti-rotation instrument device (100) further comprises of a second bulge (216) disposed on the second end (212) of the main body (110), a second removable hand grip (220), a second instrumental tip (230). A second female screw cavity (214) is disposed on the second end. The second removable hand grip (220) has a distal end (222) and proximal end (224), wherein a second channel (226) is disposed through the hand grip extending from the distal end to the proximal end, wherein a third dent (227) is disposed on the proximal end of the second removable grip and extends at least a portion of the second channel (226). A fourth dent (228) is disposed on the distal end of the first removable hand grip and is adaptive to snuggly fit second bulge (216).

The second instrumental tip (230) has a second end tip (234) and a second end (232), wherein the second end (232) has a second threading (238) disposed at the second end, wherein the threading (238) matches the second female screw cavity (214), wherein a second anti-rotation key (236) is disposed on the second instrumental tip between the first end (234) and second end (232), wherein the second anti-rotation key (236) is adaptive to snuggly fit the third dent (227) disposed on the distal end of the second removable hand grip and wherein the second threading (238) is subsequently screwed into the second female screw cavity (214) of the main handle (110) such that the second hand grip (220) is tightly sandwiched between the second instrumental tip (230) and main body (110).

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

The reference numbers recited in the below claims are solely for ease of examination of this patent application, and are exemplary, and are not intended in any way to limit the scope of the claims to the particular features having the corresponding reference numbers in the drawings.

What is claimed is:

1. An anti-rotation instrument system for medical and dental applications, the system comprising an anti-rotation instrument device (100) comprising:
   (a) a main handle (110), wherein the main handle has a first end (112) and a second end (212), wherein a first female screw cavity (114) is disposed on the first end (112);
   (b) a first removable hand grip (120), wherein the removable hand grip has a distal, end (122) and a proximal end (124), wherein a channel (126) is disposed through the hand grip extending from the distal end to the proximal end, wherein a first dent (127) is disposed on the distal end of the first removable hand grip and extends at least a portion of the channel (126), wherein the first dent (127) is a non-round dent; and
   (c) a first instrumental tip (130) having a first end (134) and a second end (132), wherein the second end (132) has a threading (138) disposed at the second end, wherein the threading (138) matches said female screw cavity (114), wherein a first anti-rotation key (136) is disposed on the first instrumental tip between the first end (134) and second end (132), wherein the anti-rotation key (136) is a non-round key, wherein the first anti-rotation key (136) is adaptive to snuggly fit the first dent (127) disposed on the distal end of the first removable hand grip;
   wherein the second end (132) of the instrumental (130) passes through the channel (126) of first hand grip (120) with the first anti-rotation key (136) securely resides within the first dent (127) disposed on the distal end of the first removable hand grip (120) and wherein the threading (138) is subsequently screwed into the first female screw cavity (114) of the main handle (110) such that the first hand grip (120) is tightly sandwiched between the first instrumental tip (130) and main body (110).

2. The instrument system of claim 1, wherein the system further comprises a washer (310) or a spring washer (320), wherein the washer (310) or spring washer (320) are disposed between the main body (110) and the hand grip (120).

3. The instrument system of claim 2, wherein the washer (310) is made of rubber or stainless steel.

4. The instrument system of claim 1, wherein the first end (134) and/or second end (132) of the instrumental tip (130) is made from surgical grade stainless steel or fiberglass or acrylic, or a combination thereof.

5. The instrument system of claim 1, wherein the first end (134) of the first instrumental tip (130) is a mirror, a dental sickle probe, a periodontal probe, or a surgical blade.

6. The instrument system of claim 1, wherein the anti-rotation key (136) is a flat key, a rectangle key, a hex key, a square key or an oval key.

7. The instrument system of claim 1, wherein the first dent (127) extends throughout of the channel (126) of the first removable hand grip (120).

8. The instrument system of claim 7, wherein the first anti-rotation key (136) has a length (137) equal to the length of the channel (130).

9. The instrument system of claim 1, wherein the main body (110) has a cylindrical shape or non-round shape.

10. The instrument system of claim 1, wherein the first removable hand grip (120) has a cylindrical shape or non-round shape.

11. The instrument system of claim 10, wherein the first removable hand grip (120) has a grip layer (129) disposed on exterior surface.

12. The instrument system of claim 11, wherein the grip (129) has a dot or line, pattern.

13. The instrument system of claim 11, wherein the grip layer (129) is made front stainless steel or rubber.

14. The instrument system of claim 1, wherein the system further comprising:
   (a) a first bulge (116) disposed on the first end (112) of the main body (110), wherein the first female screw cavity (114) passes through the first bulge;
   (b) a second dent (128) is disposed on the proximal end of the first removable grip (120), wherein the second dent (128) is adaptive to snuggly fit the first bulge (116);
   wherein the second end (132) of the instrumental tip (130) passes through the channel (126) of first hand grip (120) with the first anti-rotation key (136) securely reside within the first dent (127) disposed on the distal end of the first removable hand grip (120) and wherein the threading (138) is subsequently screwed into the first female screw cavity (114) of the main handle (110) such that the first bulge (116) is snuggly fit into the second dent of the first removable grip (120) and such that the first hand grip (120) is tightly sandwiched between the first instrumental tip (130) and main body (110).

15. An anti-rotation instrument system for medical and dental applications, the system consisting of an anti-rotation instrument device (100) consisting of:
   (a) a main handle (110), wherein the main handle consists of a first end (112) and a second end (212), wherein a first female screw cavity (114) is disposed on the first end (112);
   (b) a first removable hand grip (120), wherein the removable hand grip consists of a distal end (122) and a proximal end (124), wherein a channel (126) is disposed through the hand grip extending from the distal end to the proximal end, wherein a first dent (127) is disposed on the distal end of the first removable hand grip and extends at least a portion of the channel (126), wherein the first dent (127) is a non-round dent; and
   (c) a first instrumental tip (130) consisting of a first end (134) and a second end (132), wherein the second end (132) consists of a threading (138) disposed at the second end, wherein the threading (138) matches said female screw cavity (114), wherein a first anti-rotation key (136) is disposed on the first instrumental tip between the first end (134) and second end (132), wherein the anti-rotation key (136) is a non-round key, wherein the first anti-rotation key (136) is adaptive to snuggly fit the first dent (127) disposed on the distal end of the first removable hand grip;
   wherein the second end (132) of the instrumental tip (130) passes through the channel (126) of first hand grip (120) with the first anti-rotation key (136) securely resides within the first dent (127) disposed on the distal end of the first removable hand grip (120) and wherein the threading (138) is subsequently screwed into the first female screw cavity (114) of the main handle (110) such that the first hand grip (120) is tightly sandwiched between the first instrumental tip (130) and main body (110).

* * * * *